(12) United States Patent
Grote et al.

(10) Patent No.: US 7,655,681 B2
(45) Date of Patent: Feb. 2, 2010

(54) METHOD OF TREATING AND DIAGNOSING SLEEP DISORDERED BREATHING AND MEANS FOR CARRYING OUT THE METHOD

(75) Inventors: Ludger Grote, Viktoriagatan 34, S-411 25 Goteborg (SE); Kaj Stenlof, Hogenvagen 106, S-423 63 Torslanda (SE); Jan Hedner, Orangerigatan 4, 41266 Goteborg (SE)

(73) Assignees: Ludger Grote, Gothenberg (SE); Kaj Stenlof, Torslanda (SE); Jan Hedner, Gothenberg (SE)

( * ) Notice: Subject to any disclaimer, the term of this patent is extended or adjusted under 35 U.S.C. 154(b) by 0 days.

(21) Appl. No.: 10/598,114

(22) PCT Filed: Feb. 15, 2005

(86) PCT No.: PCT/SE2005/000196

§ 371 (c)(1),
(2), (4) Date: Jul. 3, 2007

(87) PCT Pub. No.: WO2005/077362

PCT Pub. Date: Aug. 25, 2005

(65) Prior Publication Data

US 2007/0281005 A1 Dec. 6, 2007

(30) Foreign Application Priority Data

Feb. 17, 2004 (SE) .................. 0400378

(51) Int. Cl.
*A61K 31/423* (2006.01)
*A61K 31/095* (2006.01)
*A61K 31/18* (2006.01)
*A61K 9/70* (2006.01)
*A61P 25/20* (2006.01)

(52) U.S. Cl. ............... 514/379; 514/373; 514/461; 514/469; 514/472; 514/601; 514/602; 514/709; 514/923; 424/449

(58) Field of Classification Search ........... 424/449; 514/373, 379, 923
See application file for complete search history.

(56) References Cited

U.S. PATENT DOCUMENTS 6,489,350 B1  12/2002 Benedyk

FOREIGN PATENT DOCUMENTS

WO    WO-0162243 A1    8/2001

OTHER PUBLICATIONS

LaRoche et al, "The New Antiepileptic Drugs", JAMA, 291 (5), Feb. 4, 2204, p. 605-614.*
Yoshiaki Saito, et al., "A Case of Alternating Hemiplegia of Childhood With Cerebellar Atrophy," Pediatric Neurology, vol. 19, No. 1, 1998.
Spiller HA, Dunaway MD, Cutino L. "Massive gabapentin and presumptive quetiapine overdose." *Vet Hum Toxicol.* Aug. 2002. p. 243-4. 44(4).
Berry RB, Kouchi K, Bower J, Prosise G, Light RW. "Triazolam in patients with obstructive sleep apnea." *Am. J. Respir. Crit. Care Med.*, Feb. 1995, p. 450-454, vol. 151, No. 2.
Schuld A, Kraus T, Haack M, Hinze-Selch D, Pollmächer T. "Obstructive sleep apnea syndrome induced by clonazepam in a narcoleptic patient with REM-sleep-behavior disorder." *J Sleep Res.* Dec. 1999. p. 321-2. 8(4).
Hedner J, Hedner T, Jonason J, Lundberg D. "GABA-ergic mechanisms in central respiratory control in the anesthetized rat." *Naunyn Schmiedebergs Arch Pharmacol.* 1981. p. 315-20. 317(4).
Lambert MV, Bird JM. "Obstructive sleep apnoea following rapid weight gain secondary to treatment with vigabatrin (Sabril)." *Seizure.* Jun. 1997. p. 233-5. 6(3).
Saletu A, Parapatics S, Saletu B, Anderer P, Prause W, Putz H, Adelbauer J, Saletu-Zyhlarz GM. "On the pharmacotherapy of sleep bruxism: placebo-controlled polysomnographic and psychometric studies with clonazepam." *Neuropsychobiology.* May 23, 2005. p. 214-25. 51(4).
Stremski ES, Brady WB, Prasad K, Hennes HA. "Pediatric carbamazepine intoxication." *Ann Emerg Med.* May 1995. p. 624-30. 25(5).

* cited by examiner

*Primary Examiner*—Shengjun Wang
*Assistant Examiner*—Sahar Javanmard
(74) *Attorney, Agent, or Firm*—Dickstein Shapiro LLP

(57) ABSTRACT

A method of treating or preventing Obstructive Sleep Apnea (OSA) comprises the administration of a pharmacologically effective amount of zonisamide to a patient in need thereof, with the proviso that OSA caused by external mechanical obstruction of the airways, such as by mucus, is excluded. Also disclosed is the use of zonisamide for the manufacture of a medicament useful in the treatment; a protective patch comprising zonisamide and a pharmaceutically acceptable carrier for transdermal or transmucosal administration to a person suffering from OSA; and the use of zonisamide for the manufacture of a diagnostic device, kit or composition for the diagnosis of sleep disordered breathing.

16 Claims, No Drawings

METHOD OF TREATING AND DIAGNOSING SLEEP DISORDERED BREATHING AND MEANS FOR CARRYING OUT THE METHOD

FIELD OF THE INVENTION

The present invention relates to a method of preventing, treating, and diagnosing sleep-related breathing disorders and to a means for carrying out the method.

BACKGROUND OF THE INVENTION

Sleep apnea is generally defined as an intermittent cessation of airflow at the nose and mouth during sleep. Continuous periods of apnea are termed apneic events. Their duration may vary but by convention, apneic events of at least 10 seconds in duration are considered significant. However, apneic events may extend up to 2-3 minutes and may cause complete (apnea) or partial (hypopnea) cessation of airflow. In this application the term apnea comprises hypopnea, and the term apneic event comprises hypopneic event. Apneic events, including hypopneic events, may also occur in aggregated form or appear in a complex with a general reduction of ventilation thereby generating continuous or sustained hypoventilation. This condition, in the context of the present invention, excludes obstruction by foreign objects or by material excreted by the body, such as mucus. Sleep apneas have been classified into three different types; central, obstructive and mixed. Central sleep apnea (CSA) is characterized by complete cessation of the activity of all respiratory muscles while in obstructive sleep apnea (OSA) airflow is interrupted despite continuing respiratory neural drive. OSA occurs as a result of occlusion of the upper airway, usually at the level of the oropharynx, and is the most prevalent form of sleep apnea. Mixed apnea consists of an initial central component followed by obstructive apnea. In the following CSA will not be differentiated from OSA, and will be comprised by the term OSA.

OSA spans over a wide range of upper airway flow changes with the common denominator of one or more of the following; arousal (brief awakening from sleep), alteration of tissue blood gas and pH content as well as endocrine, paracrine, hemodynamic and vascular changes. In its simplest form the condition may be characterized by subtle airflow restriction typically associated with sleep fragmentation resulting in daytime sleepiness or various degree of cognitive dysfunction as well as various symptoms suggestive on non-restorative sleep. OSA associated with daytime symptoms, specifically daytime hypersomnolence, is generally referred to as the Obstructive Sleep Apnea Syndrome (OSAS). Beside hypersomnolence, cognitive and mood changes appear to provide a substantial burden on general health in this condition. Hypersomnolence has been associated with complications including reduced working and driving performance. Moreover, cardiovascular complications, in particular hypertension, cardiac failure, myocardial infarction and stroke are common in OSA and OSA has been associated with increased insulin resistance, diabetes, obesity, changes in lipid metabolism and increased platelet aggregability. Such symptoms and complications are not confined to severe cases but also observed in cases of partial OSA and in OSA patients without apparent signs of daytime hypersomnolence.

The prevalence of OSA in the adult population depends on clinical laboratory cut-off values applied for the condition. Epidemiological studies suggest that OSA defined as an apnea-hypopnea index (number of apneas per hour of sleep) equal to or higher than 5 occurs in 24% of working adult men and in 9% of adult women. The prevalence of OSA in combination with pronounced daytime symptoms (OSAS) was observed at a rate of 4% in men and 2% in women. The prevalence of minor daytime symptoms induced by discrete sleep-related breathing disturbances is unknown. However, habitual snoring is a common phenomenon reported by 15-25% of the adult population. The patho-physiology of OSA is virtually unknown.

The principal forms of treating or preventing OSA include surgery of the upper airway, intra-oral mandibular advancement devices and long-term treatment with positive airway pressure (PAP). PAP treatment operates by the generation of a mechanical airway splint counteracting airway collapse. Although technically effective this method is hampered by poor long-term compliance due to poor tolerance and frequent side effects from airway mucous membranes. Surgery and intra-oral mandibular advancement devices are not uniformly effective. In particular surgery has been associated with a considerable relapse of symptoms also in cases with initially excellent treatment results. Various forms of pharmacological treatment, e.g. acetazolamide, tricyclic antidepressants, theophylline, progesterone, and topiramate have been employed but have not gained wide clinical use.

Thus there is a need for an improved method for treating or preventing snoring, sleep apnea and other forms of sleep disordered breathing. In particular, pharmacological treatment of such disorders would offer a definite advantage in front the invasive or non-invasive methods used at present, many of which only provide insufficient relief and some of which are cumbersome to the patient.

Zonisamide, 1,2-benzisoxazole-3-methanesulfonamide, disclosed in U.S. Pat. No. 4,513,006 is a known anti-epileptic drug; see: Peters D H and Sorkin E M. *Zonisamide. A review of its pharmacodynamic and pharmacokinetic properties, and therapeutic potential in epilepsy*. Drugs 45(5); 1993:760-87. It has also been considered as a potential anti-obesity agent and as an agent for treating neuropathic pain (U.S. Pat. No. 4,689,350). Its potential effect in the treatment of Parkinson's disease is presently investigated in clinical trials.

OBJECTS OF THE INVENTION

One object of the present invention is to provide a method of treating snoring, sleep apnea, and other forms of sleep disordered breathing that reduces and/or eliminates at least some of the drawbacks of the methods known to the art.

Another object of the present invention is to provide a means for carrying out the method according to the invention.

A further object of the present invention is to provide a method detecting the presence of OSA in a patient and a means for use in the method.

Further objects of the invention will become apparent from the following short description of the invention, a number of preferred embodiments thereof, and the appended claims.

SUMMARY OF THE INVENTION

According to the present invention is provided a method of treating or preventing snoring, sleep apnea and other forms of sleep disordered breathing, all of which are comprised by the terms Obstructive Sleep Apnea (OSA) as used herein, comprising the administration of a pharmacologically effective amount of zonisamide to a patient in need thereof, with the proviso that sleep disordered breathing caused by external mechanical obstruction of the airways, such as by mucus, is excluded.

Zonisamide has not been considered for the treatment of snoring, sleep apnea and other forms of sleep disordered breathing.

A pharmacologically effective amount of zonisamide is one that eliminates or substantially reduces the manifestations of sleep disordered breathing-related conditions over a period of sleep of from 30 minutes to 10 hours.

Zonisamide may administered by various routes. The most preferred route is by peroral administration. For this purpose a pharmacologically effective amount of zonisamide is incorporated into a tablet, a lozenge, a capsule or similar dosage form comprising a pharmaceutically acceptable carrier. Particularly preferred are peroral preparations designed for uptake through the oral mucosa, such as sublingual preparations. Also preferred is trans-dermal administration. Preparations for transdermal delivery of zonisamide are disclosed in U.S. Pat. No. 6,489,350 B1. The transdermal formulation is specifically advantageous in regard of simplicity and from a patient comfort standpoint. It may, for instance, take the form of a transdermal patch.

Peroral preparations of zonisamide, including preparations for sustained release, are known in the art and marketed in, for instance, the U.S.A. For preparing further preparations for per-oral administration reference is made to *Pharmaceutical Dosage Forms*: Tablets. Vol. 1-3, H A Lieberman et al., Eds. Marcel Dekker, New York and Basel, 1989-1990, which hereby is incorporated into this application by reference. In particular specific reference is made to chapter 7 (Special Tablets, by J W Conine and M J Pikal), chapter 8 (Chewable Tablets, by R W Mendes, O A Anaebonam and J B Daruwala), and chapter 9 (Medicated Lozenges; by D Peters).

The pharmacologically effective amount of zonisamide in oral administration for treatment of sleep disordered breathing will vary depending on factors such as the particular formulation of zonisamide used, the route of administration, the release profile of the formulation into which it is incorporated, the severity of the disease, individual pharmacokinetic and -dynamic properties as well as the status of the patient. For instance, the dose range for peroral administration of zonisamide to an adult, otherwise healthy person will be from 50 to 800 mg per 24 hours. Normally, an amount of from 100 to 400 mg of zonisamide is envisaged as the normal range used for a peroral administration in OSA. The appropriate dose range for the compound can be narrowed by titration in routine experiments. The half-life of zonisamide in plasma is about 60 hrs.

In addition to the methods of administration of the compound of the invention mentioned above also parenteral, intranasal, and rectal administration can be useful, as well as administration by inhalation.

The timing of the administration of zonisamide according to the invention will depend on the formulation and/or route of administration used. In the majority of cases zonisamide will be administered as a long-term treatment regimen, whereby pharmacokinetic steady state conditions will be reached. Medication for per oral or parenteral administration may also be given in direct relation to a particular sleeping period, for instance from 1 to 3 hours prior to the expected onset of sleep.

According to the invention Zonisamide may be combined, in one and the same pharmaceutical preparation, with other compounds that are effective in treatment of OSA or CSA.

According to a preferred aspect of the invention Zonisamide may be used for diagnosing sleep disorders related to snoring, sleep apnea or other forms of sleep-disordered breathing to dissociate them from other types of sleep disorders. The diagnostic method according to the invention comprises administrating a pharmacologically effective dose of zonisamide to a person with manifest or suspected OSA in increasing amounts prior to or during sleep. The pharmacologically effective dose may be comprised by multiple doses each of which is not pharmacologically effective, so as to provide for titration of pharmacological effect. The observation of a reduction in the severity and/or number of sleep disordered breathing events or reduced sleepiness/increased alertness during daytime following upon such administration is indicative of the presence of obstructive sleep apnea.

The invention will now be explained in more detail by reference to a preferred but not limiting embodiments.

DESCRIPTION OF PREFERRED EMBODIMENTS

Example 1

Controlled, Repeated Dosing, Repeated Withdrawal of Zonisamide

A controlled repeated dosing, repeated withdrawal study of zonisamide was undertaken in a male patient (age 62, BMI 26.5) with light to moderate OSA (A/H index, 30 and 35 on previous screening). This patient also exhibited central apneas (CSA) on both screening nights (CSA index, 5 and 6). Approximately 10% of the obstructive sleep apnea events on both screening nights had a clear mixed component. A baseline polysomographic recording (standard sleep montage, nasal pressure recording) was undertaken at baseline and zonisamide therapy was started at 100 mg o.d. orally (Zonegran® capsules) with an increase to 400 mg after two weeks and finally to 600 mg at the end of 12 weeks. Repeat sleep recordings were undertaken after 19 days (5 days on 400 mg) and after 90 days (6 days on 600 mg). The following key index data were recorded (Table 1).

TABLE 1

Key index data recorded in a repeated dosing, repeated withdrawal study

| Record | BMI | AI | HI | AHI | CSAI | MinSat | Sat <90%/hr | BP SBP/DBP | B-gluc |
|---|---|---|---|---|---|---|---|---|---|
| Day 0 | 26.5 | 16 | 22 | 38 | 8 | 82 | 4 | 165/95 | 6.7 |
| Day 19 | 26.4 | 4 | 9 | 13 | 2 | 89 | <1 | 155/89 | 6.4 |
| Day 90 | 25.6 | 2 | 6 | 8 | 2 | 90 | 0 | 145/85 | 5.9 |

Abbreviations: BMI (body mass index, $kg/m^2$), AI (apnea index, number of obstructive apneas per hour of sleep), HI (hypopnea index, number of obstructive hypopneas per hour of sleep), AHI (apnea/hypopnea index, number of obstructive apneas/hypopneas per hour of sleep), CSAI (central sleep apnea index, number of central apneas per hour of sleep), MinSat (lowest oxygen saturation value reached during the sleep recording), Sat <90/hr (number of episodes reaching an oxygen saturation below 90% per hour of sleep), BP (blood pressure), SBP (systolic blood pressure, mmHg), DBP (diastolic blood pressure, mmHg), B-gluc (blood glucose concentration, mol/L).

The number of mixed events decreased in proportion to the number of obstructive events. Polysomnographically recorded sleep variables were not systematically affected. There was no clinically significant change in total sleep time after zonisamide and the relative proportions of non-REM stage 1+2 and slow wave sleep as well as REM sleep remained unchanged. Daytime sleepiness was markedly reduced as evidenced by spontaneous reporting already after 10 days of treatment. Subjective and spouse reports verified a clear reduction of nocturnal snoring episodes soon after onset of treatment. Blood pressure and blood glucose concentration were gradually reduced starting already after 10 days of treatment. No side effects were reported during the study period.

These findings demonstrate a potent apnea reducing effect of zonisamide in sleep apneics, an effect that encompassed both obstructive and central events. Moreover, the beneficial effect on sleep apnea appeared to be maintained over a more extended time period. In addition there were effects recorded on blood pressure and blood glucose concentration suggestive of a beneficial influence on these two variables as a result of the apnea reducing effect of the drug. This effect was apparent without concomitant changes in BMI but could be improved by body weight reduction.

Example 2

Uncontrolled repeated dosing of zonisamide. An uncontrolled study of three male patients (mean BMI at baseline 32) with light to moderate/severe OSA treated with zonisamide up to an average of 177 days was performed. Polysomnography (standard sleep montage, nasal pressure recording) was undertaken at baseline. Zonisamide therapy was started at 50 or 100 mg o.d. orally (Zonegran® capsules). Dosing was gradually increased during 7 to 81 days to reach 400, 100 and 100 mg, respectively. A repeat sleep study (follow-up 1) was undertaken. A further sleep study (follow-up 2) was performed after 165, 218 and 149 days at doses of 400, 600 and 200 mg, respectively. The follow-up 2 measurements were thus performed at a pharmacokinetical steady-state. The following key index data were recorded:

TABLE 2a-d

Key index data recorded in a repeated dosing study

| Pat. ID | Zoni dose | TOT | BMI | AHI | Sat. min |
|---------|-----------|-----|------|-----|----------|
| a) Baseline | | | | | |
| BW | 0 | 0 | 31.4 | 12 | 86 |
| MS | 0 | 0 | 35.0 | 57 | 79 |
| RA | 0 | 0 | 28.3 | 20 | 88 |
| b) Follow-up 1 | | | | | |
| BW | 400 | 81 | 30.7 | 3 | 91 |
| MS | 100 | 10 | 35.1 | 59 | 80 |
| RA | 100 | 7 | 28.3 | 12 | 85 |
| c) Follow-up 2 | | | | | |
| BW | 400 | 165 | 29.3 | 3 | 90 |
| MS | 600 | 218 | 33.5 | 53 | 78 |
| RA | 200 | 149 | 27.9 | 11 | 90 |
| d) Mean for all patients | | | | | |
| Baseline | 0 | 0 | 32 | 30 | 84 |
| Follow-up 1 | 200 | 33 | 31 | 25 | 85 |
| Follow-up 2 | 400 | 177 | 30 | 22 | 86 |

Abbreviations. Zonisamide dose at the time of investigation (Zoni dose); accumulated time of continuous zonisamide treatment at the time of the investigation irrespective of dose titration scheme (TOT); lowest oxygen saturation value reached during the sleep recording (Sat Min).

Mean AHI was reduced from 30 to 25 at follow-up 1 and further to 22 at follow-up 2. Two patients responded considerably better than the third to this therapy. Sat Min was changed in accordance with the change in AHI. Average BMI diminished gradually from 32 to 30 during the study. Polysomnographically recorded sleep variables were not systematically affected. An overall positive effect on daytime sleepiness was noted, based on spontaneous reporting by the patients. No significant side effects were reported. Patient BW (number 1) underwent an additional simplified sleep recording (8 channels ventilatory monitoring during sleep) during the early titration phase at a dosing of 50 mg zonisamide, a BMI of 31.3 and an AHI of 8.

A potent apnea reducing effect of zonisamide was reconfirmed in sleep apneics. This effect was maintained over an extended time period. The effect was manifest at various dosing levels from below 100 mg and higher. It was maintained up to the dosing level of 600 mg daily, the highest level investigated.

Example 3

Sublingual tablet. 100 g of zonisamide (A; 60 mesh crystals) is blended with 80 g of Avicel PH 102 (B), 150 g of Fast-Flo lactose (C), 2 g of Cab-O-Sil (D), 0.5 g of magnesium stearate (E), 0.2 g of glycyrrhizin (F), and 5 mg of aspartame (G) for the production of 450 mg direct-compression tablets. (A), (B), (C) are blended for 20 min in a P-K blender; (F) and (G) are added, and blending is continued for 5 min; (D) and (E) are added, and blending is continued for 5 min. The powder is compressed into 500 mg tablets using $7/16$-inch standard concave tooling.

Example 4

Diagnosis of sleep disordered breathing. Sleep disordered breathing of the kind comprised by the present invention is detected by administration to a person suspected of suffering from this condition, followed by registration of one or several parameters that characterize OSA, in particular AI (apnea index, number of obstructive apneas per hour of sleep), HI (hypopnea index, number of obstructive hypopneas per hour of sleep), AHI (apnea/hypopnea index, number of obstructive apneas/hypopneas per hour of sleep), CSAI (central sleep apnea index, number of central apneas per hour of sleep), or a combination of two or more thereof. A statistically significant effect on one or several of these parameters is indicative of the presence of OSA.

The invention claimed is:

1. A method of treating Obstructive Sleep Apnea (OSA) including Central Sleep Apnea (CSA), comprising snoring, sleep apnea and other forms of sleep disordered breathing, that comprises the administration of a pharmacologically effective amount of zonisamide to a patient in need thereof, with the proviso that said snoring, sleep apnea, and sleep disordered breathing caused by external mechanical obstruction of the airways, such as by mucus, is excluded.

2. The method of claim 1, wherein said therapeutically effective dose is effective during a substantial portion of a single sleep period.

3. The method of claim 2, wherein said substantial portion is 50% or more of said sleep period.

4. The method of claim 2, wherein said substantial portion is 80% or more of said sleep period.

5. The method of claim 2, wherein said single sleep period is from one hour to ten hours.

6. The method of claim 1, wherein the administration is peroral.

7. The method of claim 6, wherein the administration is sublingual.

8. The method of claim 1, wherein the administration is topical.

9. The method of claim 6, wherein the administration is confined to the frontal portion of the neck and the breast.

10. The method of claim 6, wherein the therapeutically active dose is released from a composition for controlled release over a period of time extending from 1 hour to 12 hours and more.

11. The method of claim 1, wherein from 50% to 100% of said therapeutically effective dose is released within a period of three hours from administration.

12. The method of claim 1, wherein from 80% to 100% of said therapeutically effective dose is released within a period of five hours from administration.

13. The method of claim 10, wherein said therapeutically effective dose is from 50 to 800 mg.

14. A protective patch comprising zonisamide in an amount therapeutically effective in the treatment of Obstructive Sleep Apnea (OSA) including Central Sleep Apnea (GSA), comprising snoring, sleep apnea and other forms of sleep disordered breathing, and a pharmaceutically acceptable carrier for transdermal or transmucosal administration, with the proviso that snoring, sleep apnea, and sleep disordered breathing caused by external mechanical obstruction of the airways, such as by mucus, is excluded.

15. The method of claim 1, comprising the administration of one or more additional compounds effective in the treatment of GSA or GSA.

16. The patch of claim 14, comprising one or more additional compounds effective in the treatment of GSA or GSA.

* * * * *